United States Patent
Shin et al.

(10) Patent No.: US 10,132,768 B2
(45) Date of Patent: Nov. 20, 2018

(54) GAS SENSOR AND METHOD FOR MANUFACTURING SAME

(71) Applicants: SK INNOVATION CO., LTD., Seoul (KR); UNIST (ULSAN NATIONAL INSTITUTE OF SCIENCE AND TECHNOLOGY), Ulsan (KR)

(72) Inventors: Heung-Joo Shin, Ulsan (KR); Yeong Jin Lim, Busan (KR); Jeong Il Heo, Gyeonggi-do (KR)

(73) Assignees: SK INNOVATION CO., LTD., Seoul (KR); UNIST (ULSAN NATIONAL INSTITUTE OF SCIENCE AND TECHNOLOGY), Ulsan (KR)

( * ) Notice: Subject to any disclaimer, the term of this patent is extended or adjusted under 35 U.S.C. 154(b) by 188 days.

(21) Appl. No.: 14/895,702

(22) PCT Filed: Aug. 29, 2014

(86) PCT No.: PCT/KR2014/008080
§ 371 (c)(1),
(2) Date: Dec. 3, 2015

(87) PCT Pub. No.: WO2015/030528
PCT Pub. Date: Mar. 5, 2015

(65) Prior Publication Data
US 2016/0169824 A1    Jun. 16, 2016

(30) Foreign Application Priority Data

Aug. 30, 2013  (KR) .................... 10-2013-0104283
Sep. 2, 2013   (KR) .................... 10-2013-0104584

(51) Int. Cl.
*G01N 27/12*  (2006.01)
*G01N 33/00*  (2006.01)

(52) U.S. Cl.
CPC .......... *G01N 27/12* (2013.01); *G01N 27/125* (2013.01); *G01N 27/127* (2013.01); *G01N 33/0027* (2013.01)

(58) Field of Classification Search
CPC .... G01N 27/12; G01N 27/127; G01N 27/125; G01N 27/126
See application file for complete search history.

(56) References Cited

FOREIGN PATENT DOCUMENTS

| KR | 1020050108646 | 11/2005 |
|----|---------------|---------|
| KR | 1020090084318 | 8/2009  |

(Continued)

OTHER PUBLICATIONS

Tonezzer, M., et al., "Integrated zinc oxide nanowires/carbon microfiber gas sensors", Sensors and Actuators B 150 (Sep. 15, 2010) 517-522.*

*Primary Examiner* — Paul West
(74) *Attorney, Agent, or Firm* — IP & T Group LLP

(57) ABSTRACT

Provided is a method for manufacturing a gas sensor according to an exemplary embodiment of the present invention including: a) forming a pair of photoresist electrodes spaced apart from each other and a photoresist wire connecting upper portions of the pair of photoresist electrodes to each other by exposing and developing a first photoresist coated on a substrate; b) forming a pair of carbon electrodes and a carbon wire that are connected to be integrated with each other, by pyrolyzing the pair of photoresist electrodes and the photoresist wire; and c) forming metal oxide nanowires on a surface of the carbon wire.

13 Claims, 10 Drawing Sheets

(56) References Cited

FOREIGN PATENT DOCUMENTS

| | | | |
|---|---|---|---|
| KR | 100929025 | | 11/2009 |
| KR | 1020120121511 | | 11/2012 |
| KR | 20130033939 | * | 4/2013 |
| KR | 1020130033939 | | 4/2013 |

* cited by examiner

GAS SENSOR AND METHOD FOR MANUFACTURING SAME

This application is a national stage application of PCT/KR2014/008080 filed on Aug. 29, 2014, which claims priorities of Korean patent application number 10-2013-0104283 filed on Aug. 30, 2013 and Korean patent application number 10-2013-0104584 filed on Sep. 2, 2013. The disclosure of each of the foregoing applications is incorporated herein by reference in its entirety.

TECHNICAL FIELD

The present invention relates to a gas sensor and a method for manufacturing the same, and more specifically, to a gas sensor capable of having excellent sensitivity, and having excellent electrical contact between a nanowire detecting gas and electrodes, and being mass-produced at a low price by simple processes, and a method for manufacturing the same.

BACKGROUND ART

In accordance with increase of interest in environmental issues and development of info-communication equipment, sensors for various gases have been developed in recent years. By grafting the sensors with semiconductor technology, it is easy to manufacture the sensors, and the manufactured sensors have improved performance. A primary goal of all sensors is to increase sensitivity for improving performance, and an effort to achieve this goal has also been increased.

Meanwhile, since a semiconductor-type gas sensor in the related art includes a semiconductor thin film as a sensing material, there is limitation in sensitivity. For example, it is almost impossible to sense stable chemical materials such as carbon dioxide ($CO_2$).

Accordingly, in the sensor for sensing harmful gases such as carbon monoxide (CO), carbon dioxide, and the like, an electrochemical method using a conductive method of a solution, an optical method by infrared absorption, and a method for measuring electrical resistance of nanoparticles or nanowire have been applied.

The electrochemical method is to measure current flowing in external circuits by electrochemically oxidizing or reducing target gas, or to use electromotive force generated from ions in gas phase dissolved or ionized in an electrolyte solution or a solid, acting on an ionic electrode, which has disadvantages in that a reaction rate is extremely low, gas sensing range and environment for using the sensor are limited, and the cost is also high.

In addition, the optical method by infrared absorption has an advantage to be rarely affected by other mixed gases or humidity; however, it has disadvantages such as a complicated device, a large size, and high cost.

In general, a chemical sensor has a structure for sensing gas by contact combustion, such that when the gas reacts with the sensor including a platinum wire as a catalyst, the sensor is capable of sensing the gas by using change in resistance of the platinum wire by endothermic reaction or exothermic reaction, to thereby have improved stability and sensitivity.

Meanwhile, as the relationship between contact reaction by chemical adsorption of a gas and electron density has been identified and an oxide semiconductor-type gas sensor has been recently developed and commercialized, the semiconductor-type gas sensor has been developed to be capable of sensing most gases including a combustible gas, which achieves miniaturization, cost reduction and improvement in reliability as compared to gas sensors according to other schemes.

As compared to other sensors that are required to be heated up to about 300° C. to detect nitrogen oxide, and the like, a gas sensor using carbon nanotube as one of the semiconductor-type gas sensor has an advantage in that sensitivity thereof is thousands of times higher than those of other sensors since the carbon nanotube is possible to be operated even at room temperature, and has nano-sized particles.

A gas sensor of measuring change in electrical resistance of a nanoparticle itself or a material coating the nanoparticle according to concentration of a gas to be measured, has been developed. When the nanoparticles are used, an area ratio to volume is significantly high, such that an effect into change in resistance with respect to total volume of an effect of a surface reaction according to change in gas concentration is significantly large, thereby making it possible to manufacture a sensor having significantly high sensitivity.

As described in Korean Patent No. 10-0655640 (Dec. 4, 2006), in the sensor using the nanoparticles or the nanowires according to the related art, electrical resistance is measured by connecting electrodes capable of measuring change in electrical resistance of nanomaterials only at specific portions by non-uniformly dispersing the nanomaterials on the surface, or flowing the nanomaterials on pre-patterned electrodes, or by using electrophoresis to be in contact with electrodes.

The above-mentioned semiconductor-type gas sensor according to the related art has disadvantages in that physical and electrical connection between the nanomaterials and the electrodes is unstable, and the nanomaterials being in contact with the surface are affected by the surface in a gas sensing process.

Afterward, a suspended nanowire-based sensor is manufactured by adhering a nanowire onto electrodes spaced apart from the surface at a predetermined interval, that is, having a post shape by electrophoresis, or selectively growing the nanowires from one electrode to the opposite electrode. The existing suspended nanowire-based sensor has good sensitivity, but has poor contact between the nanowire and the electrodes, difficulty in controlling a manufacturing process, and requires high cost in manufacturing the sensor and long time for manufacturing the sensor. Therefore, the sensor has limitation in commercialization for mass-production of the sensor.

DISCLOSURE

Technical Problem

An object of the present invention is to provide a gas sensor in which a carbon wire having excellent physical and chemical properties and functional metal oxide nanowires are integrated with each other, wherein electrical conductivity of the metal oxide nanowires is changed depending on gas concentration, and a method for manufacturing the same.

In addition, in order to solve problems of a nanowire-based gas sensor attached on a substrate according to the related art, that is, reduction in sensitivity and a noise problem due to affects of the substrate, another object of the present invention is to provide a gas sensor in which the carbon wire is spaced apart from the substrate at a predetermined interval, metal oxide nanowires which are gas sensing materials are grown on a surface of the carbon wire to be free from the affects of the substrate, and a method for manufacturing the same.

Here, two carbon electrodes and the carbon wire are manufactured in an integrated form so that contact between the carbon wire spaced apart from the substrate and the two carbon electrodes supporting the carbon wire is physically and electrically stabilized, and two carbon electrodes are electrically connected to each other only through the carbon wire, such that change in resistance between two carbon electrodes is put under the control of change in resistance of the metal oxide nanowires coating the carbon wire.

In addition, another object of the present invention is to provide a gas sensor in which the metal oxide nanowires are radially grown on the surface of the carbon wire, such that gas to be measured is easily accessed to the surfaces of the metal oxide nanowires, thereby easily manufacturing a hierarchical nanostructure capable of increasing performance of the gas sensor, and a method for manufacturing the same.

Further, another object of the present invention is to provide a gas sensor in which the position, the number, the structure, and the like, of the carbon wire, are capable of being freely controlled, the metal oxide nanowires are capable of being coated (grown) locally on the surface of the carbon wire or around the carbon wire, and mass-production thereof is achieved at a low price with remarkably high productivity, and a method for manufacturing the same.

In addition, another object of the present invention is to provide a method for manufacturing a gas sensor capable of relieving thermal stress generated at the time of pyrolyzing the exposed and developed photoresist to be stably manufactured in a finer structure.

Technical Solution

In one general aspect, a method for manufacturing a gas sensor, the method includes: a) forming a pair of photoresist electrodes spaced apart from each other and a photoresist wire connecting upper portions of the pair of photoresist electrodes to each other by exposing and developing a first photoresist coated on a substrate; b) forming a pair of carbon electrodes and a carbon wire that are connected to be integrated with each other, by pyrolyzing the pair of photoresist electrodes and the photoresist wire; and c) forming metal oxide nanowires on a surface of the carbon wire.

The method may further include: after step b) and before step c), d) forming a photoresist sacrificial layer covering the pair of carbon electrodes and exposing the carbon wire by coating a second photoresist on the substrate on which the pair of carbon electrodes and the carbon wire are formed and exposing and developing the second photoresist.

Step a) may include: a1) forming an insulating layer etching mask in which an insulating layer region positioned in a sensing region is exposed, the sensing region being a region at which the carbon wire is formed, by coating a 1-1-th photoresist on the substrate on which an insulating layer is formed and exposing and developing the 1-1-th photoresist; a2) removing the insulating layer region positioned in the sensing region using the insulating layer etching mask, and removing the insulating layer etching mask; a3) forming a concave portion groove by partially etching the substrate positioned in the sensing region using the insulating layer from which the insulating layer region positioned in the sensing region is removed, as a substrate etching mask; and a4) coating the first photoresist on the substrate in which the concave portion groove is formed.

Step c) may include: c1) forming a metal oxide seed on the surface of the carbon wire; and c2) forming the metal oxide nanowires on the surface of the carbon wire by growing the metal oxide seed.

Step c1) may be performed by a coating method of applying a solution including a metal oxide precursor, an atomic layer deposition method of atomic layer-depositing a metal oxide, a physical deposition method of depositing a metal oxide by sputtering, or an oxidation method of oxidizing a metal deposited after depositing the metal, on at least one surface of the carbon wire.

Step c2) may include: growing monocrystal metal oxide nanowires from the metal oxide seed by inserting the carbon wire on which the metal oxide seed is formed into an autoclave including a metal oxide aqueous solution and heating the autoclave.

Step c2) may include: contacting the metal oxide precursor with the carbon wire, and then growing monocrystal metal oxide nanowires from the seed by Joule heat generated from the carbon wire.

Step a) may include: coating the first photoresist on the substrate; exposing the first photoresist by using an electrode forming photomask having a shape corresponding to a pair of electrodes facing each other and spaced apart from each other; re-exposing the first photoresist using a wire forming photomask having a wire shape so that upper portions of a pair of exposure regions exposed by the electrode forming photomask are connected to an exposure region exposed by the wire forming photomask; and forming a pair of photoresist electrodes spaced apart from each other and forming a photoresist wire connecting upper portions of the pair of photoresist electrodes to each other, by developing the re-exposed first photoresist.

In the re-exposing of the first photoresist, a surface region of the first photoresist may be partially exposed.

The photoresist wire may have any one shape selected from the group consisting of linear single wire or array in which a plurality of wires are assembled, mesh, and honey comb.

In another general aspect, a gas sensor includes: a pair of carbon electrodes facing each other and spaced apart from each other on an insulating substrate; a carbon wire integrated with the pair of carbon electrodes and connecting upper portions of the pair of carbon electrodes; and metal oxide nanowires bound to a surface of the carbon wire to radially protrude.

The substrate may have a concave portion groove formed in a sensing region, the sensing region being a region at which the carbon wire is positioned.

The metal oxide nanowires may be selectively formed on the surface of the carbon wire.

The metal oxide nanowires may be monocrystal.

A metal oxide of the metal oxide nanowires may be one or two or more selected from the group consisting of zinc oxide (ZnO), copper oxide (CuO), indium oxide ($In_2O_3$) and tin oxide ($SnO_2$).

A metal oxide of the metal oxide nanowires may cover the surface of the carbon wire corresponding to 80 to 100% based on total surface area of the carbon wire.

The metal oxide nanowire may have a length of 10 nm to 5 μm.

Advantageous Effects

The gas sensor and the method for manufacturing the same according to the present invention have the following.

The suspended conductive carbon wire may be simply and collectively manufactured by single photoresist coating, subsequent exposure process and pyrolysis process at a low price.

In addition, the carbon wire and the carbon electrodes are simultaneously formed in an integrated form, such that the gas sensor in which electrical connection is complete may be achieved without additional further processes for improving physical and electrical contact of the carbon electrodes and the carbon wire.

Further, forms of the carbon wire are determined by shapes of a photomask of the exposure process, an amount of exposing energy, and the pyrolysis process. An interval between the carbon wire and the substrate is determined by whether or not a concave portion groove is formed, a height of the photoresist, and the pyrolysis process. Therefore, the suspended carbon wire may be freely formed in various structures.

In addition, the interval between the carbon wire and the substrate may be increased by formation of the concave portion groove, such that gas sensing area may be increased, and thermal stress may be minimized at the time of forming the carbon electrodes and the carbon wire by pyrolysis.

Further, the carbon wire structure is formed by reduction of volume according to pyrolysis of the photoresist in a microunit, such that the nanostructure may be manufactured at a low price without using high priced equipment for nanoprocesses.

In addition, due to differentiated volume reduction generated according to heights of the electrodes during the pyrolysis process, tensile stress may be generated in the carbon wire, and the tensile stress may prevent deformation of the carbon wire which may occur by liquid phase external environment.

Further, the metal oxide nanowires which are gas sensing materials are grown by Joule heat of the carbon wire, such that the metal oxide nanowires may be locally grown only on the surface of the carbon wire. In addition, a size of the carbon wire is small, such that temperature of the carbon wire may be easily increased even with small electric energy.

Further, electrical connection of two carbon electrodes supporting the carbon wire is formed only by the carbon wire and the metal oxide nanowires, such that change in electrical conductivity of the metal oxide nanowires due to change in gas concentration may be easily measured by change in resistance between two carbon electrodes.

In addition, since the metal oxide nanowires are grown on the surface of the carbon wire spaced apart from the substrate at a predetermined interval, the metal oxide nanowires may be free from affects of the substrate such as temperature of a substrate, pollutants, a stagnant layer, and the like, to thereby increase sensitivity of the sensor.

In addition, since the carbon wire is spaced apart from the substrate, the metal oxide nanowires may be grown on the entire surface of the carbon wire, and may be grown in a form in which the metal oxide nanowires are radially spread on the carbon wire, and accordingly, contact areas of gas to be sensed and the metal oxide nanowires may be maximized to increase sensitivity of the gas sensor.

Further, the metal oxide nanowires are selectively formed only on a region of the carbon wire, such that accuracy, reproducibility, and sensitivity for detecting the gas may be increased.

[Detailed Description of Main Elements]

Figure 1:
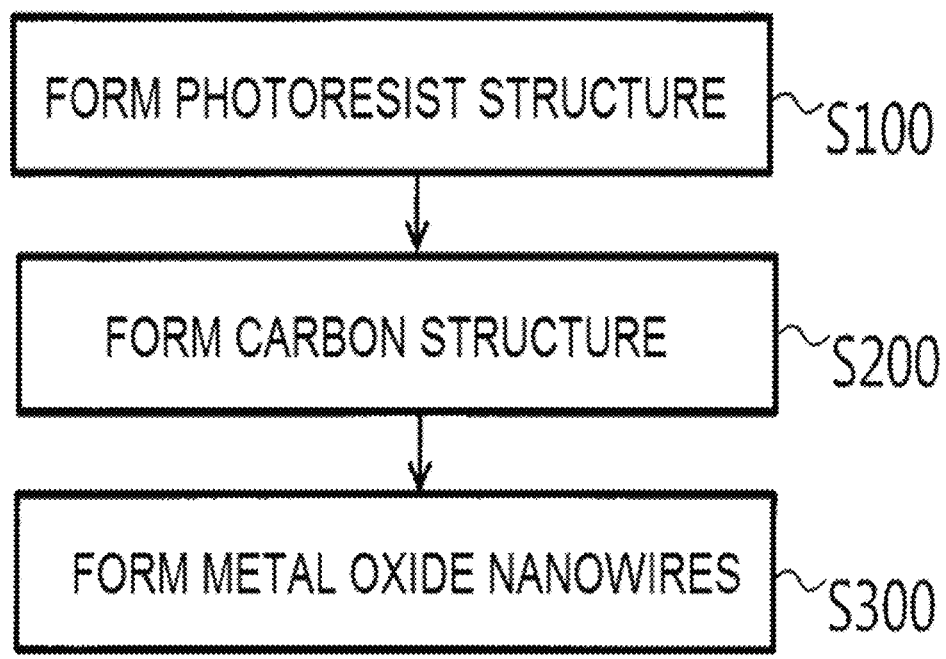
FIG. 1 is a process diagram illustrating a method for manufacturing a gas sensor according to an exemplary embodiment of the present invention.

| | |
|---|---|
| 10: Substrate | 11: Insulating Layer |
| 20: Photoresist Electrode | 21: Carbon Electrode |
| 30: Photoresist Wire | 31: Carbon Wire |
| 40: Metal Oxide Seed | 41: Metal Oxide Nanowire |
| H: Concave Portion Groove | |

Best Mode

Hereinafter, a gas sensor and a method for manufacturing the same of the present invention will be described in detail with reference to the accompanying drawings. The exemplary embodiments of the present invention to be described below are provided by way of example so that the idea of the present invention can be sufficiently transferred to those skilled in the art to which the present invention pertains. Therefore, the present invention may be implemented in many different forms, without being limited to the drawings to be described below. The drawings may be exaggerated in order to specify the spirit of the present invention. Like reference numerals denote like elements throughout the specification.

Meanwhile, unless technical and scientific terms used herein are defined otherwise, they have meanings understood by those skilled in the art to which the present invention pertains. Known functions and components will be omitted so as not to obscure the description of the present invention with unnecessary detail.

FIG. 1 is a process diagram illustrating a method for manufacturing a gas sensor according to an exemplary embodiment of the present invention. As illustrated in FIG.

1, the method for manufacturing a gas sensor according to an exemplary embodiment of the present invention may include: forming a photoresist structure including a pair of photoresist electrodes spaced apart from each other and a photoresist wire connecting upper portions of the pair of photoresist electrodes to each other by exposing and developing a first photoresist coated on a substrate S100; forming a carbon structure including a pair of carbon electrodes and a carbon wire that are connected to be integrated with each other, by pyrolyzing the pair of photoresist electrodes and the photoresist wire S200; and forming metal oxide nanowires on a surface of the carbon wire S300.

The substrate may serve as a support body physically supporting the carbon electrodes and the carbon wire to be manufactured. In addition, the substrate may be an insulating substrate including an insulating layer formed on at least one surface thereof or may be made of insulating materials per se, so as not to have an effect on currents or voltages detected though the carbon electrodes and the carbon wire.

In detail, the substrate may have a wafer shape or a film shape, and may be a rigid substrate or a flexible substrate in view of physical property. In view of crystallography, the substrate may be a monocrystal, a polycrystal or amorphous body, or may be a mixed phase in which crystalline phase and amorphous phase coexist. When the substrate is a multilayer substrate in which two or more layers are stacked, respective layers may be each independently the monocrystal, the polycrystal, the amorphous body, or the mixed phase.

In view of a material, the substrate may be an inorganic substrate including a semiconductor or an insulating organic substrate. As non-limiting examples, the substrate may be a semiconductor substrate, and the semiconductor substrate may be a multilayer substrate in which respective layers made of a material selected from Group IV semiconductor including silicon (Si), germanium (Ge) or silicon germanium (SiGe), Group III-V semiconductor including gallium arsenide (GaAs), indium phosphide (InP) or gallium phosphide (GaP), Group II-VI semiconductor including cadmium sulfide (CdS) or zinc telluride (ZnTe), Group IV-VI semiconductor including lead sulfide (PbS) or two or more materials thereof are stacked. Here, as described above, the semiconductor substrate may be a substrate including the insulating layer formed on the surface thereof. The semiconductor substrate and the insulating layer may be formed by using general methods known in the art such as thermal oxidation, deposition, and the like. The insulating layer may include silicon oxide, hafnium oxide, aluminum oxide, zirconium oxide, barium-titanium complex oxide, yttrium oxide, tungsten oxide, tantalum oxide, zinc oxide, titanium oxide, tin oxide, barium-zirconium composite oxide, silicon nitride, silicon oxynitride, zirconium silicate, hafnium silicate, mixtures thereof and composites thereof, but the materials forming the insulating layer are not limited thereto. As specific examples, the semiconductor substrate may include a semiconductor substrate (including wafer) such as a silicon (Si) substrate, a silicon (Si) semiconductor substrate on which a surface oxide layer is formed or a semiconductor substrate (including wafer) on which a semiconductor oxide layer such as a silicon on insulator (SOI) substrate is stacked, a SOI semiconductor substrate on which the surface oxide layer is formed, and the like.

However, when the inorganic substrate is made of an insulating material, the inorganic substrate made of the insulating material itself is capable of being directly used. As non-limiting examples of the insulating inorganic substrate, the insulating inorganic substrate may include silicon oxide, hafnium oxide, aluminum oxide, zirconium oxide, barium-titanium complex oxide, yttrium oxide, tungsten oxide, tantalum oxide, zinc oxide, titanium oxide, tin oxide, barium-zirconium composite oxide, silicon nitride, silicon oxynitride, zirconium silicate, hafnium silicate, mixtures thereof and composites thereof, but the materials forming the insulating inorganic substrate are not limited thereto.

The organic substrate may be a rigid organic substrate or a flexible organic substrate having insulation property. As non-limiting examples, the organic substrate may include polyethylene terephthalate (PET), polyethylene naphthalate (PEN), polyimide (PI), polycarbonate (PC), polypropylene (PP), triacetyl cellulose (TAC), polyethersulfone (PES), polydimethylsiloxane (PDMS) or a polymer substrate containing mixtures thereof.

The step of forming a pair of photoresist electrodes spaced apart from each other and a photoresist wire connecting upper portions of the pair of photoresist electrodes to each other by exposing and developing the first photoresist coated on the substrate S100, may include: coating a first photoresist on a substrate; exposing the first photoresist by using an electrode forming photomask having a shape corresponding to a pair of electrodes facing each other and spaced apart from each other; re-exposing the first photoresist using a wire forming photomask having a wire shape so that upper portions of a pair of exposure regions exposed by the electrode forming photomask are connected to an exposure region exposed by the wire forming photomask; and forming a pair of photoresist electrodes spaced apart from each other and forming a photoresist wire connecting the pair of photoresist electrodes to each other, by developing the re-exposed first photoresist.

When the substrate includes the insulating layer, the first photoresist may be coated onto the surface on which the insulating layer is formed, and materials and coating methods of the photoresist are not limited but are usable as long as they are generally used in a field for manufacturing a semiconductor device. As non-limiting examples, the coating of the first photoresist may be performed by methods used to coat photoresist in a general photolithography process, for example, spin coating, and the like, but the methods of coating the photoresist are not limited thereto. After coating the photoresist, the coated photoresist layer may be dried (by soft baking), selectively, by hard baking.

The first photoresist may be made of a polymer material in which resistance to chemical agents is changed by light used in a general lithography process, and may include a negative photoresist which is insoluble to the chemical agents by exposing the photoresist to light or a positive photoresist which is soluble to the chemical agents by exposing the photoresist to light. As specific examples, the first photoresist may be a negative photoresist such as SU-8.

The electrode forming photomask may be a photomask perforated to have a shape, a structure, a size corresponding to those of pre-designed electrodes (a pair of electrodes). The first photoresist may be exposed by using the electrode forming photomask, such that an exposure region having a size, a structure, a shape corresponding to those of pre-designed electrodes may be formed in the first photoresist. Light used for the exposure may be a light of an extreme ultraviolet (EUV) region to an ultraviolet (UV) region, specifically, ultraviolet ray. At the time of exposing the photoresist, the exposing may be sufficiently performed so that change in resistance to the chemical agents is uniformly performed from a surface of the photoresist up to an interface with the substrate, by light.

After exposing the first photoresist by using the electrode forming photomask, a step of re-exposing the first photoresist using a wire forming photomask having a wire shape so that a pair of exposure regions exposed by the electrode forming photomask are connected to an exposure region exposed by the wire forming photomask may be performed.

The first photoresist may be provided with regions (hereinafter, referred to as exposure regions for the pair of electrodes) exposed in a shape corresponding to a pair of electrodes facing each other and spaced apart from each other by perforated shapes, that is, design of the photomask by the exposing using the electrode forming photomask. The wire forming photomask may be a photomask perforated in a wire shape, connecting the exposure regions for the pair of electrodes to each other. Specifically, the perforated shapes of the wire forming photomask may have a shape selected from the group consisting of linear single wire, single wire array, mesh, and honey comb.

By re-exposing the first photoresist using the wire forming photomask, the exposure regions for the pair of electrodes, and a wire-shaped exposure region at which exposure regions for the pair of electrodes and both ends of the exposure regions for the pair of electrodes are connected to each other may be formed in the first photoresist. Here, the wire-shaped exposure region may have a shape corresponding to perforated shapes of the wire forming photomask.

Light used for re-exposing may be a light of an extreme ultraviolet (EUV) region to an ultraviolet (UV) region, specifically, ultraviolet ray, which is independent from light used in the exposing using the electrode forming photomask. Light energy in the exposing may be controlled so that change in resistance to chemical agents by light is performed only on a surface layer of the first photoresist. That is, at the time of re-exposing the first photoresist, the surface of the first photoresist may be partially exposed up to a predetermined depth, such that at the time of developing the first photoresist, a suspended photoresist wire of which both ends are supported by the photoresist electrode may be manufactured.

After the exposing using the electrode forming photomask and the re-exposing using the wire forming photomask are performed, a developing process may be performed to remove the remaining photoresist except for the exposure regions. The developing of the first photoresist may be performed by using a developing solution used in general photolithography processes.

The pair of photoresist electrodes spaced apart from each other and the photoresist wire connecting the pair of photoresist electrodes to each other may be formed on the substrate by the developing of the first photoresist. Here, the photoresist wire may have a shape selected from the group consisting of linear single wire, single wire array, mesh, and honey comb, and both ends of the photoresist wire may contact surfaces of the uppermost portions of the pair of photoresist electrodes to each other. Specifically, the photoresist wire and the uppermost portions of the photoresist electrodes may be integrally connected to each other, which is caused by forming the photoresist wire connecting the pair of photoresist electrodes to each other by exposing and re-exposing the same first photoresist.

Then, a step of forming a carbon structure including a pair of carbon electrodes and a carbon wire that are connected to be integrated with each other, by pyrolyzing the photoresist structure including at least one pair of photoresist electrodes and the photoresist wire S200 may be performed.

That is, the pair of photoresist electrodes and the photoresist wire formed on the substrate may be pyrolyzed to form the carbon electrodes and the carbon wire. Here, the pair of photoresist electrodes spaced apart from each other and the photoresist wire may be carbonized by pyrolysis, the carbon wire having a diameter of 50 nm to several micrometers (μms) and a length of several micrometers (μms) to hundreds of micrometers (μms) may be manufactured, and an interval between the substrate and the carbon wire may be 1 micrometer (μm) to tens of micrometers (μms). Pyrolysis may be performed under a vacuum state or under inert gas atmosphere at a temperature of 800° C. or more. Since the pair of photoresist electrodes and the photoresist wire are integrally connected to each other, the pyrolysis allows the pair of photoresist electrodes and the photoresist wire to be pyrolyzed to form the pair of photoresist electrodes and the carbon wire that are connected to be integrated with each other.

After forming the carbon structure S200, a step of forming metal oxide nanowires on the surface of the carbon wire S300 may be performed.

In detail, the forming of the metal oxide nanowires may include: forming a metal oxide seed on the surface of the carbon wire; and forming the metal oxide nanowires on the surface of the carbon wire by growing the metal oxide seed.

A metal oxide of the metal oxide nanowire may be a material in which electrical conductivity is changed depending on concentration of a gas to be detected. As specific examples, the metal oxide of the metal oxide seed may be one or two or more selected from the group consisting of zinc oxide (ZnO), copper oxide (CuO), indium oxide ($In_2O_3$) and tin oxide ($SnO_2$), and independently, the metal oxide of the metal oxide nanowires may be one or two or more selected from the group consisting of zinc oxide (ZnO), copper oxide (CuO), indium oxide ($In_2O_3$) and tin oxide ($SnO_2$). Preferably, the metal oxide seed provides a nucleus generating and growing place for growing the metal oxide to be monocrystal in a nanowire shape, and therefore, the metal oxide seed and the metal oxide nanowires may be made of the same material.

The forming of the metal oxide seed may be performed by a coating method of applying a solution including a metal oxide precursor and performing heat treatment, an atomic layer deposition method of atomic layer-depositing a metal oxide, a physical deposition method of depositing a metal oxide by sputtering, or an oxidation method of oxidizing a metal deposited after depositing the metal, on at least one surface of the carbon wire.

In detail, the forming of the metal oxide seed may be performed by physical deposition or chemical deposition. The physical deposition or the chemical deposition may include sputtering, magnetron-sputtering, electron beam evaporation (E-beam evaporation), thermal evaporation, laser molecular beam epitaxy (L-MBE), pulsed laser deposition (PLD), vacuum deposition, atomic layer deposition (ALD), plasma enhanced chemical vapor deposition (PECVD), and the like, but the physical deposition or the chemical deposition of the present invention is not limited thereto. Here, the metal oxide seed may be integrally coated on the surface of the carbon wire by deposition, or a metal thin film may be deposited and then oxidized to form the metal oxide seed.

Independently from the forming of the seed using the above-described deposition, the forming of the seed may be performed by a coating method of applying the solution including the metal oxide precursor and performing heat treatment to coat the metal oxide seed on the surface of the carbon wire. The coating method may economically form a seed coating layer on the surface of the carbon wire by a significantly simple method of immersing the substrate into the solution and heating the substrate, which provides industrial advantages.

In detail, when the coating method is used, the substrate including the carbon wire is immersed into the solution capable of forming nanoparticles of the metal oxide to be grown, wherein the nanoparticles of the metal oxide are coated on the substrate by heating the solution for a predetermined time. As specific examples, when it is attempted to form a zinc oxide seed, the solution may be a solution including zinc acetate ($Zn(CH_3CO_2)_2$) and sodium hydroxide (NaOH) to coat zinc oxide nanoparticles.

Then, a step of forming the metal oxide nanowires on the surface of the carbon wire by growing the metal oxide seed may be performed.

The forming of the metal oxide nanowires may include: contacting the metal oxide precursor with the carbon wire, and then growing monocrystal metal oxide nanowires from the seed by Joule heat generated from the carbon wire.

In the forming of the metal oxide nanowires, the metal oxide precursor may be in contact with the carbon wire, and then the monocrystal metal oxide nanowires may be manufactured from the seed by Joule heat generated from the carbon wire.

That is, by flowing a current in the carbon wire through the carbon electrodes, the metal oxide nanowires may be manufactured from the seed by Joule heat generated from the carbon wire. When the Joule heat is generated by flowing the current in the carbon wire through the carbon electrodes, only the temperature of the carbon wire may be selectively increased. Even though the metal oxide seed is formed on the surface of the carbon electrodes by selective heating, only the seed positioned on the surface of the carbon wire may be locally grown to be the metal oxide nanowires.

In detail, two electrodes supporting the carbon wire are electrically connected to each other only by the carbon wire in a micro size or a nano size, and due to the small size of the carbon wire has a small size, high electrical resistance is high and thermal transfer to the outside is limited, and accordingly, when voltages are applied to two carbon electrodes, Joule heat is generated by the current flowing through the carbon wire, such that only the temperature of the carbon wire may be effectively increased, and the metal oxide nanowires may be grown only on the surface of the carbon wire by using the Joule heat.

When the metal oxide nanowires are formed by physical deposition or chemical deposition, the forming of the metal oxide nanowires and the forming of the metal oxide seed may be performed by a single deposition process.

In the forming of the metal oxide nanowires, the metal oxide precursor may be in a solution phase. In detail, the forming of the metal oxide nanowires may include: inserting the carbon wire on which the metal oxide seed is formed into an autoclave including a metal oxide aqueous solution, and then heating the autoclave to grow monocrystal metal oxide nanowires from the seed.

The substrate provided with the carbon wire in which a coating layer of the metal oxide seed is formed may be immersed into the autoclave including the solution in which the metal oxide precursor is dissolved, and then the metal oxide nanowires which are gas sensing materials may be selectively grown on the surface of the carbon wire by Joule heat caused by applying predetermined voltages to two carbon electrodes. This method is capable of forming the monocrystal metal oxide nanowires having excellent crystallinity from the metal oxide seed, and is capable of radially forming the metal oxide nanowires covering the surface of the carbon wire and having uniform size.

A material of the metal oxide nanowires may be the same as that of the metal oxide seed, and the metal oxide of the metal oxide nanowires may be one or two or more selected from the group consisting of zinc oxide (ZnO), copper oxide (CuO), indium oxide ($In_2O_3$) and tin oxide ($SnO_2$). As a specific example thereof, when the metal oxide nanowires are made of zinc oxide, the solution in which the metal oxide precursor is dissolved may be an aqueous solution including $Zn(NO_3)_2$ and hexamethylenetetramine (HMTA). However, the present invention is not limited in view of metal oxide precursor solution used at the time of forming the metal oxide nanowires.

Accordingly, the metal oxide nanowires in which electrical conductivity is changed depending on concentration of a gas are radially formed on the surface of the carbon wire, wherein the concentration of the gas may be appreciated by measuring change in values of current flowing by applying voltages to two carbon electrodes. When zinc oxide nanowires are used, various gases such as $C_2H_5OH$, $NO_2$, $H_2$, $H_2S$, CO, $O_2$, $NH_3$, and the like, may be detected.

Figure 2:
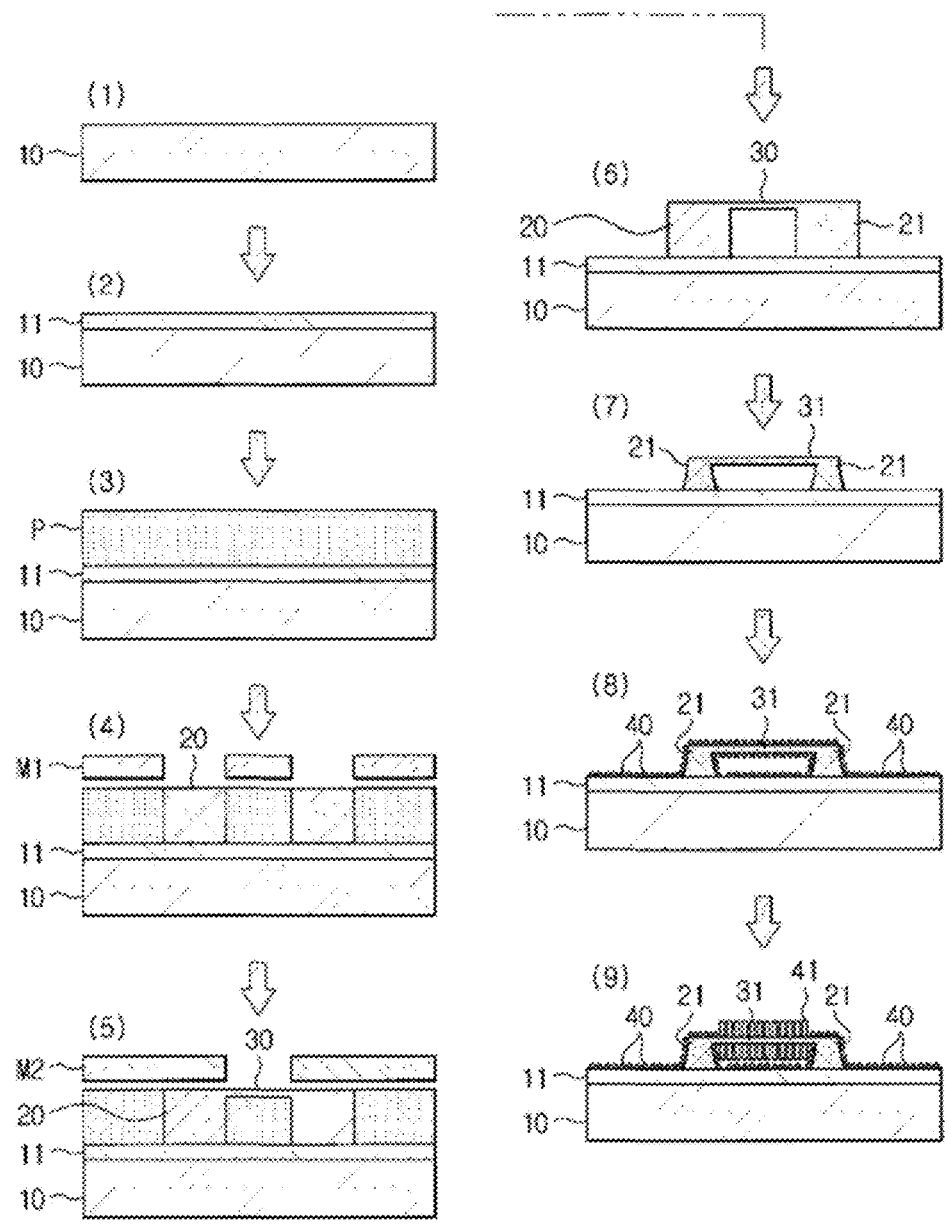
FIG. 2 is another process diagram illustrating a method for manufacturing a gas sensor according to an exemplary embodiment of the present invention.
Figure 3:
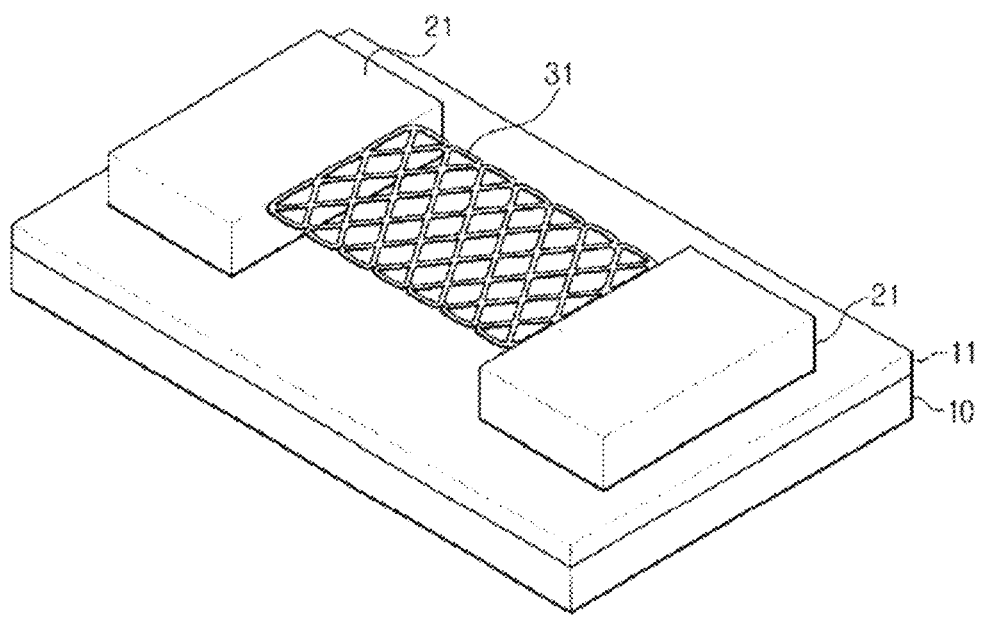
FIG. 3 is a perspective view illustrating the gas sensor manufactured according to an exemplary embodiment of the present invention.
Figure 4:
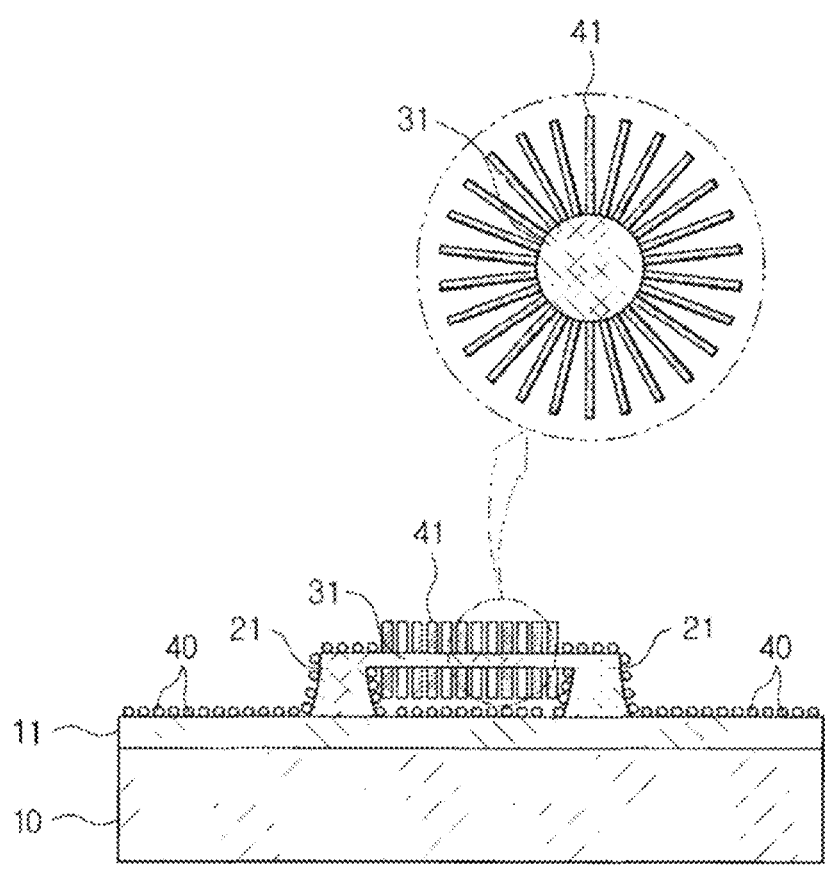
FIG. 4 is a cross-sectional view illustrating the gas sensor manufactured according to an exemplary embodiment of the present invention, and a detailed cross-sectional view illustrating a cross section of the carbon wire having the metal oxide nanowires formed thereon.

FIG. 2 is a process diagram illustrating a method for manufacturing a gas sensor according to an exemplary embodiment of the present invention, FIG. 3 is a cross-sectional view illustrating a configuration of the gas sensor completed according to an exemplary embodiment of the present invention, and FIG. 4 is a detailed cross-sectional view illustrating a concave portion of the gas sensor completed according to an exemplary embodiment of the present invention.

When describing the present invention based on FIGS. 2 to 4, in the case of a semiconductor substrate such as silicon, the manufacturing method according to an exemplary embodiment of the present invention forms an insulating layer 11 on an upper surface of the substrate 10. When the substrate is silicon, the insulating layer 11 may be made of insulating materials such as silicon dioxide, silicon nitride, and the like.

Then, a photoresist P1 is primarily applied onto an upper surface of the substrate 10 on which the insulating layer 11 is formed. That is, the photoresist P1 may be applied on the insulating layer 11 formed on the upper surface of the substrate 10.

Here, the photoresist P1 may be applied by uniform coating, large area coating, spin coating for a short processing time. Here, although FIG. 2 illustrates that the photoresist P1 is negative photoresist such as SU-8, the photoresist is not limited thereto, but may be positive photoresist.

Primary exposing may be performed by positioning a first photomask M1 in which corresponding electrode regions are perforated on an upper portion of the insulating layer 11 to which the photoresist P1 is applied, and irradiating UV.

In the primary exposing, it is preferable to sufficiently irradiate UV light energy so that the photoresist P1 is capable of being cured from an uppermost portion of the photoresist up to just above the insulating layer 11.

After the primary exposing is completed, the photoresist P1 is cured on the upper portion of the insulating layer 11 in a shape of the corresponding electrode regions by perforations of the first photomask M1.

A pair of photoresist electrodes 20 spaced apart form each other are formed on the upper surface of the substrate 10 as described above, and as a next step, a re-exposing process of forming a photoresist wire connecting upper portions of the pair of photoresist electrodes spaced apart from each other, may be performed.

Here, the photoresist wire 30 may connect the pair of photoresist electrodes 20 formed on the upper surface of the substrate 10 and spaced apart from each other, and more detailed description thereof is described as follows.

Secondary-exposing (re-exposing) may be performed by positioning a second photomask M2 perforated in corresponding wire shape on the upper portion of the substrate 10 to which the photoresist P is applied, and using UV. Here, the perforations in the corresponding wire shape may be formed in a shape of linear single wire, single wire array, mesh, and honey comb, and it is preferable to control UV light energy at the time of exposing the photoresist so that only the uppermost portion of the photoresist P is capable of being cured in a wire shape.

Then, the remaining photoresist P except for portions exposed by the primary and secondary exposing may be removed by development, thereby forming a photoresist structure including the pair of photoresist electrodes 20 spaced apart from each other and the photoresist wire 30 connecting the upper portions of the pair of photoresist electrodes 20 to each other.

Next, pyrolysis may be performed on the photoresist structure to manufacture a carbon structure. In detail, the pair of photoresist electrodes 20 and the photoresist wire 30 may be pyrolyzed to be converted into the carbon electrodes 21 and the carbon wire 31 connecting the upper portions of the carbon electrodes 21, respectively. By pyrolysis of the photoresist wire 30, a carbon body in a wire shape, having a diameter of 50 nm to several micrometers ($\mu$m) and a length of several micrometers ($\mu$m) to hundreds of micrometers ($\mu$m) may be manufactured, and an interval between the substrate and the wire, that is, a height of the carbon electrode 21 may be 1 micrometer ($\mu$m) to tens of micrometers ($\mu$m).

Figure 5:
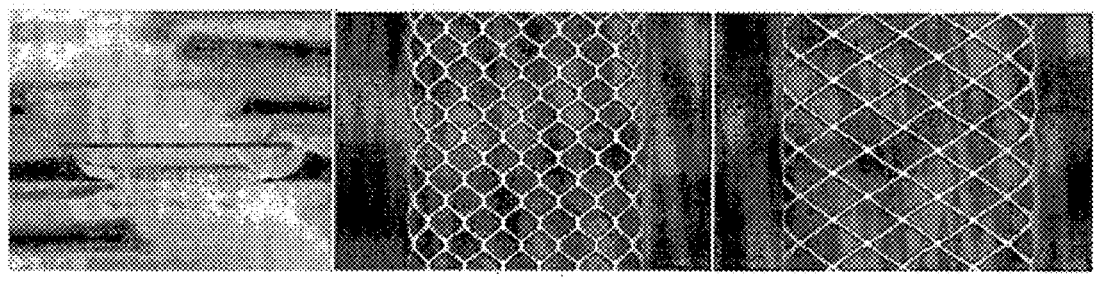
FIG. 5 is scanning electron microscope (SEM) images of a carbon electrode and a carbon wire manufactured according to an exemplary embodiment of the present invention.

Here, the carbon wire may be formed in a mesh shape or a honey comb shape as illustrated in FIG. 3 or FIG. 5. When describing the carbon wire based on the mesh shape or the honey comb shape, the photoresist structure may be described as the photoresist electrodes 20 and a photoresist perforated net connecting the upper portions of the pair of photoresist electrodes 20 to each other, and after pyrolysis, may be described as the carbon electrodes 21 and a carbon perforated net connecting the upper portions of the pair of carbon electrodes 21. Here, pores of the perforated net may have a polygonal shape such as a square (including rhombus, rectangle, square, and the like), hexagonal or octagonal shape.

The pyrolysis may be preferably performed under a vacuum state or under inert gas atmosphere at a temperature of 800° C. or more.

When the pair of photoresist electrodes 20 and the photoresist wire 30 are converted into the carbon electrodes 21 and the carbon wire 31, the metal oxide nanowires 41 may be formed on the surface of the converted carbon wire 31 to complete a gas sensor.

Here, the metal oxide of the metal oxide nanowires 41 may be a metal oxide in which electrical conductivity is changed depending on gas concentration, and may be one or two or more selected from the group consisting of zinc oxide (ZnO), copper oxide (CuO), indium oxide ($In_2O_3$) and tin oxide ($SnO_2$). The metal oxide nanowire 41 may be grown by impregnating the substrate with an aqueous solution containing the metal oxide precursor and raising a temperature of the substrate.

In detail, as illustrated in FIG. 2, the metal oxide seed may be formed on at least one portion of the surface of the carbon wire 31, and then the metal oxide seed positioned on the surface of the carbon wire 31 may be grown to radially form the metal oxide nanowires 41. Here, the metal oxide nanowires 41 may have a length of tens to hundreds of nanometers, but may be appropriately controlled in consideration of usage of the sensor, environment in which the sensor is used, kinds of gas to be sensed, and the like.

At the time of forming the seed, the substrate having the carbon structure formed thereon is immersed into a solution capable of forming nanoparticles of the metal oxide to be grown, here, a metal oxide seed coating layer may be formed by heating a temperature of the solution for a predetermined time to coat the nanoparticles of the metal oxide on the surface of the carbon structure. In the case of zinc oxide, the solution for coating the zinc oxide nanoparticles may include a methanol solution containing zinc acetate and sodium hydroxide.

The formation of the seed by the solution immersion and heating is a significantly simple and low-cost process, which provides industrial advantages since the process is significantly and easily controlled and maintained, and processing time is also short. The metal oxide seed may be formed by the solution by immersion and heating on all exposed surfaces of the substrate as illustrated in FIG. 2, but when the seed is grown by Joule heat generated from the carbon wire, only the seed positioned on the surface of the carbon wire is possible to be selectively grown, and therefore, adverse effect on the sensor is not significant. That is, when voltages are applied between two carbon electrodes supporting the carbon wire, remarkably high Joule heat is generated in the carbon wire having nano to micro dimension, and the carbon electrodes themselves may not be substantially heated, and accordingly, only the seed positioned on the surface of the carbon wire may be selectively grown.

However, as described above, the metal oxide seed may be coated on a desired surface by integrally coating a metal oxide, using chemical vapor deposition such as an atomic layer deposition or physical vapor deposition such as sputtering, or may be coated by performing vapor deposition on the metal thin film and oxidizing the metal thin film to coat the metal oxide seed layer on the desired surface.

In a state in which the carbon wire 31 is heated by Joule heat generated from the carbon wire 31, caused by applying voltages to two carbon electrodes 21, the metal oxide seed 31 may be grown to be the metal oxide nanowires 41 by supplying the metal oxide precursor. As a specific example, the substrate coated with the metal oxide nanoparticles (the metal oxide seed) is immersed into an autoclave including an aqueous solution including the metal oxide precursor, and then the metal oxide nanowires 41 which are gas sensing materials may be selectively grown on the surface of the carbon wire 31 by Joule heat caused by applying predetermined voltages to two carbon electrodes 21. Examples of zinc oxide may include an aqueous solution including zinc nitride ($Zn(NO_3)_2$) and hexamethylenetetramine (HMTA) for growth of zinc oxide nanowires.

In particular, when the metal oxide seed is formed on at least one surface of the carbon wire, and then the substrate is immersed into the aqueous solution including the metal oxide precursor, and the metal oxide nanowire is grown by Joule heat generated from the carbon wire, the metal oxide nanowires having uniform and regular size may be manufactured over the entire surface of the carbon wire, and the metal oxide nanowires may have a remarkably isotropic radial structure.

Figure 6:
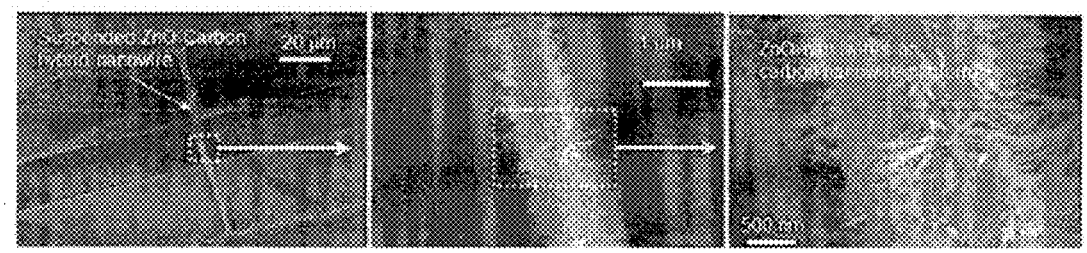
FIG. 6 is scanning electron microscope (SEM) images of the gas sensor manufactured according to an exemplary embodiment of the present invention.

In detail, as illustrated in FIG. 4 or FIG. 6, when the substrate is immersed with the aqueous solution including the metal oxide precursor and voltages are applied to the carbon electrodes, the material for growing the metal oxide seed may be significantly and uniformly supplied, and as illustrated in the cross-sectional view of the carbon wire provided as the detailed view of FIG. 4, the metal oxide nanowires may have significantly uniform size, and may have a remarkably isotropic radial structure based on the carbon nanowire.

Figure 7:
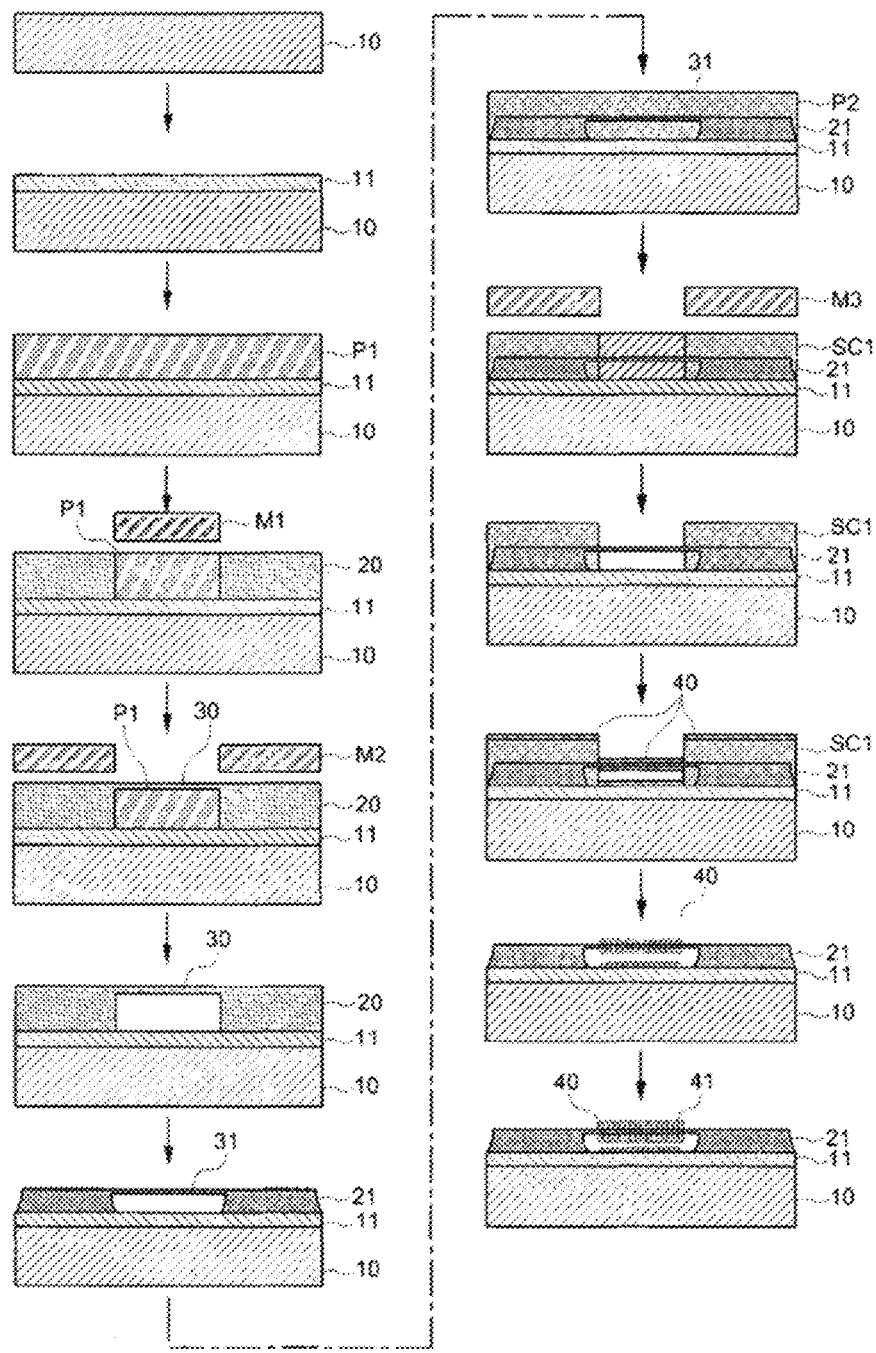
FIG. 7 is another process diagram illustrating a method for manufacturing a gas sensor according to an exemplary embodiment of the present invention.

FIG. 7 is a view illustrating another process of the manufacturing method according to an exemplary embodiment of the present invention. As illustrated in FIG. 7, in the method for manufacturing a gas sensor according to an exemplary embodiment of the present invention, after the performing of the pyrolysis and before the forming of the metal oxide nanowires 41, a step of forming a photoresist sacrificial layer SC1 covering the pair of carbon electrodes 21 and exposing the carbon wire 31 by coating a second photoresist P2 on the substrate 10 on which the pair of carbon electrodes 21 and the carbon wire 31 are formed and exposing and developing the second photoresist, may be further performed.

In detail, a second photoresist layer may be formed by coating the second photoresist P2 on the substrate 10 on which the pair of carbon electrodes 21 and the carbon wire 31 are formed. A material and a coating method of the second photoresist may be any material for photoresist and any coating methods for photoresist as long as they are generally used in fields for manufacturing a semiconductor device. As non-limiting examples, the coating of the second photoresist may be performed by methods used to coat photoresist in a general photolithography process, for example, spin coating, and the like, but the methods of coating the photoresist are not limited thereto. After coating the photoresist, the coated photoresist layer may be dried (by soft baking), selectively, by hard baking.

The second photoresist P2 may be made of a polymer material in which resistance to chemical agents is changed by light used in a general lithography process, and may include a negative photoresist which is insoluble to chemical agents by exposing the photoresist to light or a positive photoresist which is soluble to the chemical agents by exposing the photoresist to light. As specific example, the second photoresist P2 may be positive photoresist such as AZ.

A photomask (a photomask for a sacrificial layer, M3) used for exposing the second photoresist P2 may be a photomask with perforations having a size and a shape corresponding to a sensing region, the sensing region being a substrate region between two carbon electrodes 21 facing each other and spaced apart from each other, that is, a region at which the carbon wire 31 is positioned. Here, as described below, the photoresist sacrificial layer SC1 manufactured by exposing and developing the second photoresist P2 limits a region at which the metal oxide seed is formed to a surface region of the carbon wire, and accordingly, the photoresist sacrificial layer SC1 may have the same length as or a shorter length than that of the carbon wire 31 in a direction in which two carbon electrodes 21 are spaced apart from each other, and when the length of the carbon electrode 21 in a direction vertical to the direction in which two carbon electrodes 21 are spaced apart from each other is determined as a width of the carbon electrode 21, the photoresist sacrificial layer SC1 may have the same length as or a similar length to the width of the carbon electrode 21.

By exposing and developing the second photoresist P2 by using the above-described photomask for a sacrificial layer M3, the photoresist sacrificial layer SC1 covering the pair of carbon electrodes 21 and exposing the carbon wire 31 may be formed. Here, the exposing of the second photoresist P2 may be performed by light of an extreme ultraviolet (EUV) region to an ultraviolet (UV) region, specifically, ultraviolet rays. The developing of the second photoresist P2 may be performed by using a developing solution used in general photolithography processes.

Then, a step of forming the metal oxide seed on the carbon wire 31 exposed to the surface by the photoresist sacrificial layer SC1, and then removing the photoresist sacrificial layer SC1, or a step of forming the metal oxide seed and completing growth of the metal, oxide nanowires, and then removing the photoresist sacrificial layer SC1 may be performed. Since descriptions of the forming of the metal oxide seed and the growing of the metal oxide nanowires are similar to those as described above, descriptions thereof will be omitted.

After the coating layer of the metal oxide seed is formed on the surface of the carbon wire exposed by the photoresist sacrificial layer SC1, or the metal oxide nanowires are formed, a step of removing the photoresist sacrificial layer SC1 may be performed. The removing of the photoresist sacrificial layer SC1 may be performed by using a photoresist etching solution generally used in fields for manufacturing a semiconductor device or by physical methods such as lift-off.

Figure 8:
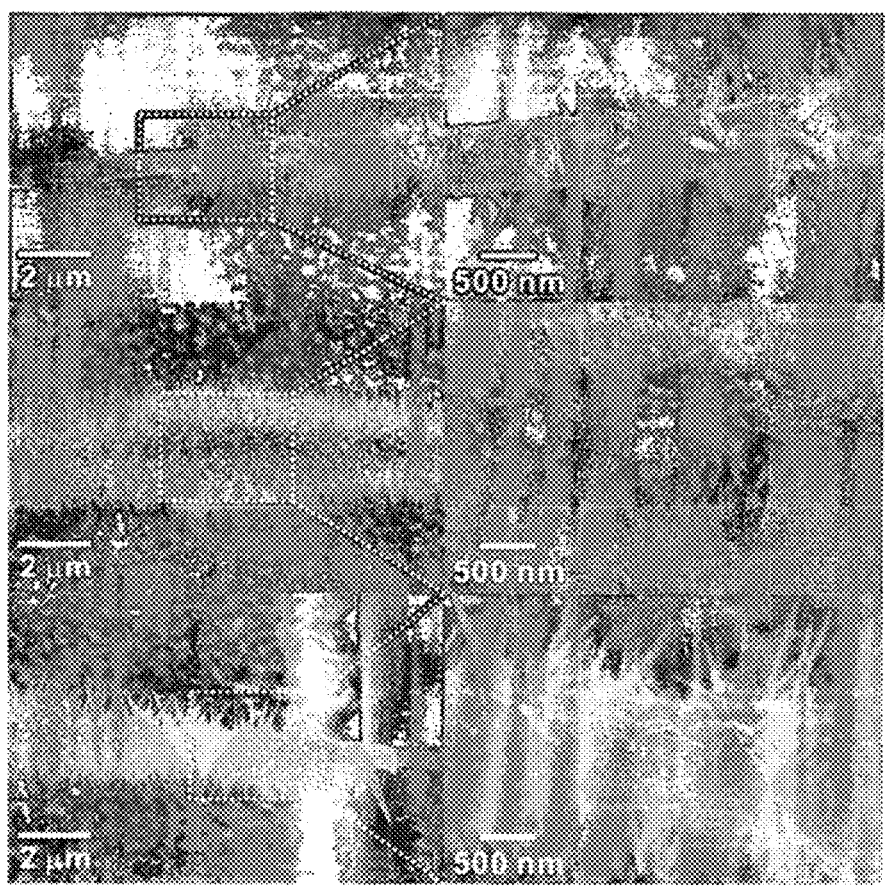
FIG. 8 is scanning electron microscope (SEM) images obtained by observing a left edge, the center, and right edge of the carbon wire having the metal oxide nanowires formed thereon in the gas sensor manufactured according to an exemplary embodiment of the present invention.

FIG. 8 illustrates one example of a sensor manufactured by forming the photoresist sacrificial, layer SC1, forming zinc oxide seed by using RF-sputtering, removing the photoresist sacrificial layer SC1, and growing the seed to the nanowires.

Figure 9:
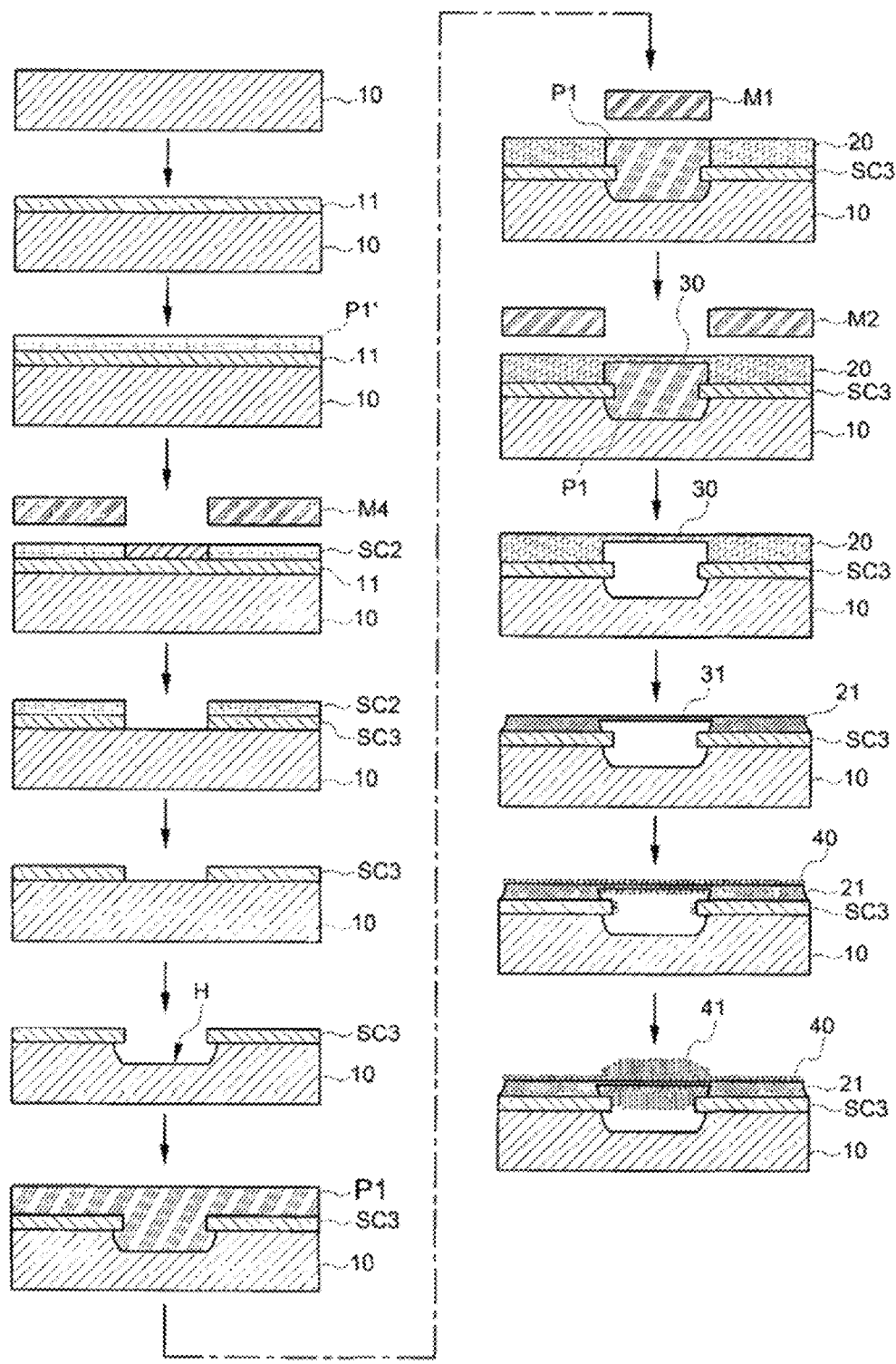
FIG. 9 is another process diagram illustrating a method for manufacturing a gas sensor according to an exemplary embodiment of the present invention.

FIG. 9 is a view illustrating another process diagram of a manufacturing method according to an exemplary embodiment of the present invention, wherein the method for manufacturing the gas sensor according to an exemplary embodiment of the present invention may further include forming a concave portion groove H in the sensing region being the substrate region on which the carbon wire 31 is positioned.

Specifically, the method may further include forming an insulating layer etching mask SC2 in which an insulating layer region positioned in the sensing region is exposed by coating a 1-1-th photoresist P1' on the substrate 10 on which the insulating layer 11 is formed and exposing and developing the 1-1-th photoresist; removing the insulating layer region positioned in the sensing region using the insulating layer etching mask SC2, and removing the insulating layer etching mask SC2; forming a concave portion groove H by partially etching the substrate 10 positioned in the sensing region using the insulating layer from which the insulating layer region positioned in the sensing region is removed, as a substrate etching mask SC3; and coating the first photoresist P1 on the substrate 10 in which the concave portion groove H is formed. Here, as described above, the substrate on which the insulating layer is formed may be a semiconductor substrate in which the insulating layer is formed. In addition, after the forming of the concave portion groove H, a step of forming the insulating layer 11' on the concave portion groove H may be further performed to strengthen insulation property of the substrate. The insulating layer 11' may be formed by heat-treating the substrate in the presence of oxygen to form a thermal oxide film. However, methods for forming the insulating layer 11' of the present invention are not limited thereto.

A material and a coating method of the 1-1-th photoresist P1' may be any material for photoresist and any coating methods for photoresist as long as they are generally used in fields for manufacturing a semiconductor device. As non-limiting examples, the coating of the 1-1-th photoresist P1' may be performed by spin coating, and the like. After coating the photoresist, the coated photoresist may be dried (by soft baking), selectively, by hard baking.

The 1-1-th photoresist P1' may be made of a polymer material in which resistance to the chemical agents is changed by light used in a general lithography process, and may include a negative photoresist which is insoluble to the chemical agents by exposing the photoresist to light or positive photoresist which is soluble to the chemical agents by exposing the photoresist to light. As specific example, the 1-1-th photoresist P1' may be positive photoresist such as AZ.

A photomask M4 used for exposing the 1-1-th photoresist P1' may be a photomask with perforations having a size and a shape corresponding to a sensing region, the sensing region being a substrate region between two carbon electrodes 21 facing each other and spaced apart from each other, that is, a region at which the carbon wire 31 is positioned. As one example, the photomask M4 may be the same as or similar to the photomask M3 used for manufacturing the photoresist sacrificial layer SC1. The exposing of the 1-1-th photoresist P1' may be performed by light of an extreme ultraviolet (EUV) region to an ultraviolet (UV) region, specifically, ultraviolet rays. The developing of the 1-1-th photoresist P1' may be performed by using a developing solution used in general photolithography processes.

By the exposing and the developing of the 1-1-th photoresist P1', the insulating layer region corresponding to a region provided with the carbon wire 31, that is, a region between two carbon electrodes 21 facing each other, is exposed to the surface of the substrate, wherein the 1-1-th photoresist P1' remaining on the substrate 10 is used as the insulating layer etching mask SC2 to remove the exposed insulating layer region. Here, the removing of the insulating layer may be performed by wet etching using an etching solution selectively dissolving materials of the insulating layer or dry etching such as plasma etching. As non-limiting examples, when the insulating layer is a silicon oxide layer, etching may be performed by hydrofluoric acid-based mixed aqueous solution. When the insulating layer region corresponding to the sensing region is removed, a portion of the substrate corresponding to the sensing region may be selectively exposed to the surface. Then, a step of removing the insulating layer etching mask SC2, and a step of forming the concave portion groove H by partially etching on the substrate positioned in the sensing region using the insulating layer remaining on the substrate, as the substrate etching mask SC3, may be performed. The etching of the substrate may be performed by wet etching using an etching solution selectively dissolving the substrate or dry etching such as plasma etching, and may be performed by wet etching for isotropic etching. As specific examples, when the substrate is a silicon (Si) substrate, wet etching may be performed by alkali etching solution including nitrate. After the substrate is partially etched, general washing step may be further performed. In addition, the above-described first photoresist P1 may be coated on the substrate 10 in which the concave portion groove H is formed. In consideration of usage of the sensor, environment in which the sensor is used, and/or target gas for detection, a depth of the concave portion groove may be appropriately controlled, and as non-limiting examples, the concave portion groove may have a depth of several micrometers (μm) to tens of micrometers (μm).

Figure 10:
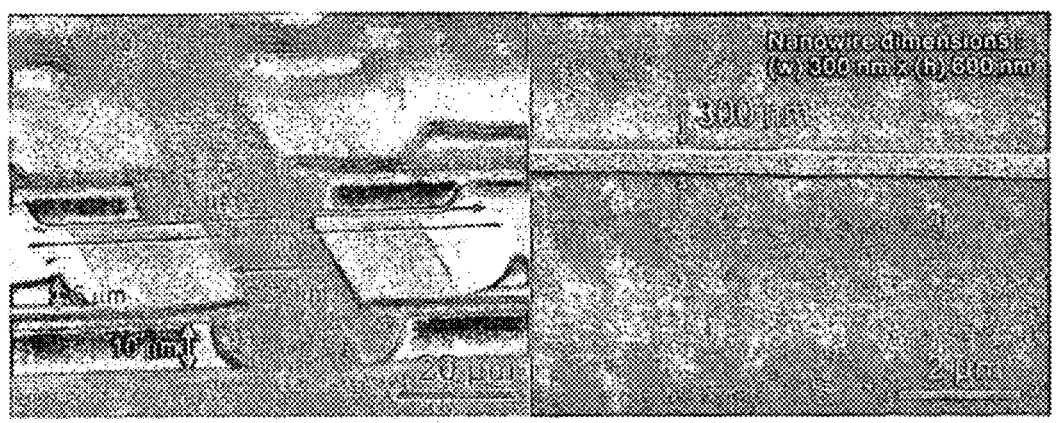
FIG. 10 is scanning electron microscope (SEM) images of the carbon electrode in which a concave portion groove is formed and the carbon wire manufactured according to an exemplary embodiment of the present invention.

FIG. 10 illustrates one example of the structure of the sensor including the pair of carbon electrodes facing each other and spaced apart from each other on the substrate in which the concave portion groove H having a depth of about 10 μm is formed, and the carbon wire connecting the upper portions of two carbon electrodes facing each other and spaced apart from each other, with the concave portion groove H interposed between two carbon electrodes. In FIG. 10, 22 μm indicates a width of the insulating layer region removed for substrate etching, and a spaced distance between two carbon electrodes facing each other and spaced apart from each other, with the concave portion groove H interposed between two carbon electrodes is 85 μm, and a height of the carbon electrode is 6 μm. When the photoresist structure is pyrolyzed, thermal stress by change in volume may occur, wherein the thermal stress may be intensified as the volume of the photoresist to be pyrolyzed is increased. Accordingly, as illustrated in FIG. 10, by decreasing the height of the carbon electrode, and securing a reaction space of the sensor reacting with the gas which is a sensing target through the concave portion groove, more sensitive and accurate sensing may be achieved, and a sensor free from thermal stress may be manufactured.

Figure 11:
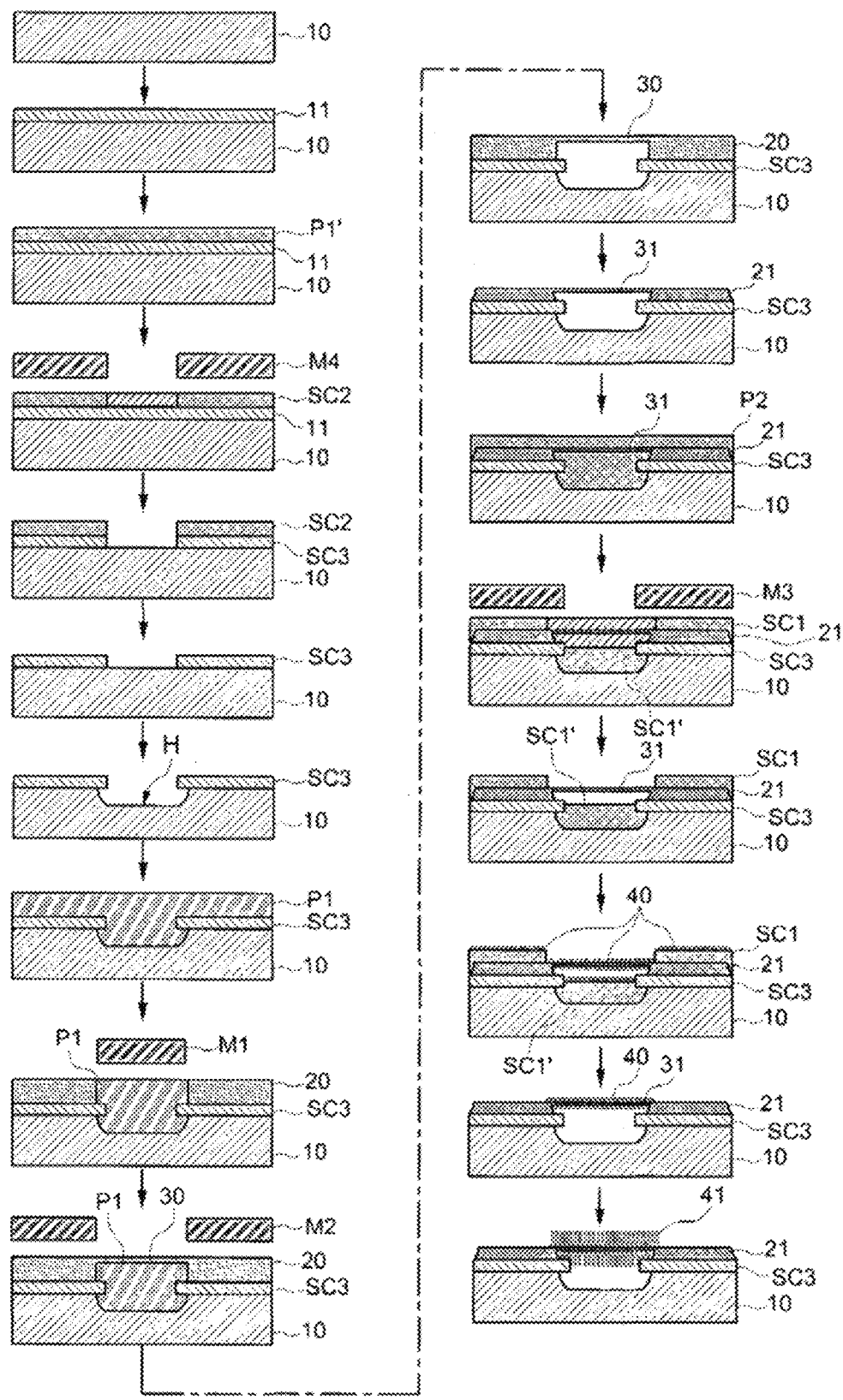
FIG. 11 is another process diagram illustrating a method for manufacturing a gas sensor according to an exemplary embodiment of the present invention.

FIG. 11 is a view illustrating another process diagram of a manufacturing method according to an exemplary embodiment of the present invention. As illustrated in FIG. 11, in the method for manufacturing a gas sensor according to an exemplary embodiment of the present invention, before the coating of the first photoresist P1, the step of forming the concave portion groove H described above on the basis of FIG. 9 may be performed, and before the forming of the metal oxide seed, the step of forming the photoresist sacrificial layer SC1 described above on the basis of FIG. 7 may be performed. Here, at the time of exposing the second photoresist P2 using the photomask for a sacrificial layer M3, the exposing is performed up to a depth at which the carbon wire 31 is positioned, but intensity of light is preferably controlled so that the second photoresist P2 which is not exposed may remain in the concave portion groove H. That is, as illustrated in FIG. 11, in the exposing of the second photoresist, intensity of light is preferably controlled so as to form a concave portion groove photoresist sacrificial layer SC1' protecting a surface of the concave portion groove H by non-exposing. The photoresist sacrificial layer SC1 manufactured by exposing and developing the second photoresist P2 may limit a region at which the metal oxide seed is formed to a surface region of the carbon wire, and the concave portion groove photoresist sacrificial layer SC1' may prevent formation of the metal oxide seed on the substrate region (sensing region) of a lower portion of the carbon wire. By exposing and developing the second photoresist P2 by using the above-described photomask for a sacrificial layer M3, the photoresist sacrificial layer SC1 covering the pair of carbon electrodes 21 and exposing the carbon wire 31 and the concave portion groove photoresist sacrificial layer SC1' covering the surface of the concave portion groove may be formed. Then, a step of forming the metal oxide seed on the carbon wire 31 exposed to the surface by the photoresist sacrificial layer SC1, and then removing the photoresist sacrificial layers SC1 and SC1', or a step of forming the metal oxide seed and completing growth of the metal oxide nanowires, and then removing the photoresist sacrificial layers SC1 and SC1' may be performed. Since descriptions of the forming of the metal oxide seed and the growing of the metal oxide nanowires are similar to those as described above, descriptions thereof will be omitted.

The present invention includes a gas sensor manufactured by the above-described manufacturing method.

As illustrated in FIGS. 2 to 11, the gas sensor according to an exemplary embodiment of the present invention may include: a pair of carbon electrodes 21 facing each other and spaced apart from each other on an insulating substrate 10; a carbon wire 31 integrated with the pair of carbon electrodes 21 and connecting upper portions of the pair of carbon electrodes; and metal oxide nanowires 41 bound to a surface of the carbon wire 31 to radially protrude.

In the gas sensor according to an exemplary embodiment of the present invention, the substrate 10 may have a concave portion groove H formed in a sensing region being a region at which the carbon wire 31 is positioned.

In the gas sensor according to an exemplary embodiment of the present invention, the metal oxide nanowires 41 may be selectively formed on the surface of the carbon wire 31.

In the gas sensor according to an exemplary embodiment of the present invention, a metal oxide of the metal oxide nanowire 41 may be a material in which electrical conductivity is changed by a target gas for detection (concentration), specifically, may be one or two or more selected from the group consisting of zinc oxide (ZnO), copper oxide (CuO), indium oxide ($In_2O_3$) and tin oxide ($SnO_2$).

In the gas sensor according to an exemplary embodiment of the present invention, the metal oxide nanowires covering the surface of the carbon wire and radially protruding may be monocrystal.

In the gas sensor according to an exemplary embodiment of the present invention, the metal oxide of the metal oxide nanowires may cover a surface of the carbon wire corresponding to 80 to 100%, specifically, 80 to 95% based on total surface area of the carbon wire.

In the gas sensor according to an exemplary embodiment of the present invention, the carbon wire may be covered by the metal oxide seed and the metal oxide nanowires. When describing the gas sensor related with the above-described manufacturing method thereof, the metal oxide nanowires are grown from the metal oxide seed formed with the coating layer on the surface of the carbon wire, and therefore, the carbon wire may be covered with the metal oxide seed which is non-grown by space restriction, and the like, and the metal oxide nanowires grown from the seed, on the surface of the carbon wire.

In the gas sensor according to an exemplary embodiment of the present invention, the target gas for detection may be one or two or more gases selected from the group consisting of $C_2H_5OH$, $NO_2$, $H_2$, $H_2S$, CO, $O_2$, $NH_3$, and the like.

In the gas sensor according to an exemplary embodiment of the present invention, the carbon wire 31 may have any one shape selected from the group consisting of linear single wire or array in which a plurality of wires are assembled, mesh, and honey comb.

In the gas sensor according to an exemplary embodiment of the present invention, a diameter and a length of the carbon wire, a spaced distance between two carbon electrodes facing each other, a depth of the concave portion groove, and the like, may be appropriately controlled in consideration of usage of the gas sensor, environment in which the sensor is used, conditions required for the sensor, and the like. As non-limiting example, the carbon wire may have a diameter of tens of nms to several μms, specifically, 50 nm to 9 μm, and may have a length of several μms to hundreds of μms, specifically, 1 μm to 900 μm. As non-limiting examples, the distance between the substrate surface and the carbon wire (a height of the carbon electrode) may be several μms to tens of μms, specifically, 1 μm to 90 μm. The depth of the concave portion groove may be several μms to tens of μms, specifically, 1 μm to 90 μm. The metal oxide nanowires may have a structure that they radially protrude on the surface of the carbon wire, based on a cross-section of the carbon wire. The metal oxide nanowires may have a size appropriate for forming a radial structure on the surface of the carbon wire. As specific and non-limiting examples, the length of the metal oxide nanowire may be tens of nms to several μms, specifically, 10 nm to 5 μm.

Hereinabove, although the present invention is described by specific matters, limited exemplary embodiments, and drawings, they are provided only for assisting in the entire understanding of the present invention. Therefore, the present invention is not limited to the exemplary embodiments. Various modifications and changes may be made by those skilled in the art to which the present invention pertains from this description.

Therefore, the spirit of the present invention should not be limited to the above-described exemplary embodiments, and the following claims as well as all modified equally or equivalently to the claims are intended to fall within the scope and spirit of the present invention.

The invention claimed is:

1. A method for manufacturing a gas sensor, the method comprising:
    forming a pair of photoresist electrodes spaced apart from each other and a photoresist wire connecting upper portions of the pair of photoresist electrodes to each other by exposing and developing a first photoresist coated on a substrate;
    forming a pair of carbon electrodes and a carbon wire that are connected to be integrated with each other, by pyrolyzing the pair of photoresist electrodes and the photoresist wire; and
    forming metal oxide nanowires on a surface of the carbon wire,
    wherein the forming of the metal oxide nanowires on a surface of the carbon wire includes:
        forming a metal oxide seed on the surface of the carbon wire; and
        forming the metal oxide nanowires on the surface of the carbon wire by growing the metal oxide seed,
    wherein the forming of the metal oxide nanowires on the surface of the carbon wire by growing the metal oxide seed includes:
        growing single crystal metal oxide nanowires from the metal oxide seed by inserting the carbon wire on which the metal oxide seed is formed into an autoclave including a metal oxide aqueous solution and heating the autoclave.

2. The method of claim 1, further comprising: after the forming of a pair of carbon electrodes and a carbon wire that are connected to be integrated with each other, by pyrolyzing the pair of photoresist electrodes and the photoresist wire and before the forming of the metal oxide nanowires on a surface of the carbon wire,
    forming a photoresist sacrificial layer covering the pair of carbon electrodes and exposing the carbon wire by coating a second photoresist on the substrate on which the pair of carbon electrodes and the carbon wire are formed and exposing and developing the second photoresist.

3. The method of claim 1, wherein the forming of a pair of photoresist electrodes spaced apart from each other and a photoresist wire connecting upper portions of the pair of photoresist electrodes to each other by exposing and developing a first photoresist coated on a substrate includes:
    forming an insulating layer etching mask in which an insulating layer region positioned in a sensing region is exposed, the sensing region being a region at which the carbon wire is formed, by coating a 1-1-th photoresist on the substrate on which an insulating layer is formed and exposing and developing the 1-1-th photoresist;

removing the insulating layer region positioned in the sensing region using the insulating layer etching mask, and removing the insulating layer etching mask;

forming a concave portion groove by partially etching the substrate positioned in the sensing region using the insulating layer from which the insulating layer region positioned in the sensing region is removed, as a substrate etching mask; and coating the first photoresist on the substrate in which the concave portion groove is formed.

4. The method of claim 1, wherein the forming of a metal oxide seed on the surface of the carbon wire is performed by a coating method of applying a solution including a metal oxide precursor, an atomic layer deposition method of atomic layer-depositing a metal oxide, a physical deposition method of depositing a metal oxide by sputtering, or an oxidation method of oxidizing a metal deposited after depositing the metal, on at least one surface of the carbon wire.

5. The method of claim 1, wherein the photoresist wire has any one shape selected from the group consisting of linear single wire or array in which a plurality of wires are assembled, mesh, and honey comb.

6. A method for manufacturing a gas sensor, the method comprising:

forming a pair of photoresist electrodes spaced apart from each other and a photoresist wire connecting upper portions of the pair of photoresist electrodes to each other by exposing and developing a first photoresist coated on a substrate;

forming a pair of carbon electrodes and a carbon wire that are connected to be integrated with each other, by pyrolyzing the pair of photoresist electrodes and the photoresist wire; and forming metal oxide nanowires on a surface of the carbon wire, wherein the forming metal oxide nanowires on a surface of the carbon wire; includes:

forming a metal oxide seed on the surface of the carbon wire; and forming the metal oxide nanowires on the surface of the carbon wire by growing the metal oxide seed, wherein the forming of the metal oxide nanowires on the surface of the carbon wire by growing the metal oxide seed; includes:

contacting a metal oxide precursor with the carbon wire, and then growing singlecrystal metal oxide nanowires from the seed by Joule heat generated from the carbon wire.

7. A method for manufacturing a gas sensor, the method comprising:

forming a pair of photoresist electrodes spaced apart from each other and a photoresist wire connecting upper portions of the pair of photoresist electrodes to each other by exposing and developing a first photoresist coated on a substrate;

forming a pair of carbon electrodes and a carbon wire that are connected to be integrated with each other, by pyrolyzing the pair of photoresist electrodes and the photoresist wire; and forming metal oxide nanowires on a surface of the carbon wire, wherein the forming a pair of photoresist electrodes spaced apart from each other and a photoresist wire connecting upper portions of the pair of photoresist electrodes to each other by exposing and developing a first photoresist coated on a substrate includes:

coating the first photoresist on the substrate;

exposing the first photoresist by using an electrode forming photomask having a shape corresponding to a pair of electrodes facing each other and spaced apart from each other;

re-exposing the first photoresist using a wire forming photomask having a wire shape so that upper portions of a pair of exposure regions exposed by the electrode forming photomask are connected to an exposure region exposed by the wire forming photomask; and forming a pair of photoresist electrodes spaced apart from each other and forming a photoresist wire connecting upper portions of the pair of photoresist electrodes to each other, by developing the re-exposed first photoresist.

8. The method of claim 7, wherein in the re-exposing of the first photoresist, a surface region of the first photoresist is partially exposed.

9. A gas sensor comprising:

a pair of carbon electrodes facing each other and spaced apart from each other on an insulating substrate;

a carbon wire integrated with the pair of carbon electrodes and connecting upper portions of the pair of carbon electrodes; and metal oxide nanowires bound to a surface of the carbon wire to radially protrude, wherein the metal oxide nanowires are selectively formed on the surface of the carbon wire, wherein a metal oxide of the metal oxide nanowires covers the surface of the carbon wire corresponding to 80 to 100% based on total surface area of the carbon wire.

10. The gas sensor of claim 9, wherein the substrate has a concave portion groove formed in a sensing region, the sensing region being a region at which the carbon wire is positioned.

11. The gas sensor of claim 9, wherein the metal oxide nanowires are monocrystal.

12. The gas sensor of claim 9, wherein a metal oxide of the metal oxide nanowires is one or two or more selected from the group consisting of zinc oxide (ZnO), copper oxide (CuO), indium oxide ($In_2O_3$) and tin oxide ($SnO_2$).

13. The gas sensor of claim 9, wherein the metal oxide nanowires have a length of 10nm to 5 μm.

* * * * *